United States Patent [19]

Zasloff et al.

[11] Patent Number: 5,192,756
[45] Date of Patent: Mar. 9, 1993

[54] AMINOSTEROL ANTIBIOTIC

[75] Inventors: Michael Zasloff, Merion; Karen Moore, Lansdowne; Suzanne Wehrli, Bala Cynwyd, all of Pa.

[73] Assignee: The Children's Hospital of Pennsylvania, Philadelphia, Pa.

[21] Appl. No.: 853,634

[22] Filed: Mar. 18, 1992

[51] Int. Cl.$^5$ .......................... A61K 31/56; C07J 41/00
[52] U.S. Cl. ...................................... 514/182; 552/521
[58] Field of Search ......................... 552/521; 514/182

[56] References Cited

U.S. PATENT DOCUMENTS 3,308,116 3/1967 deRuggieri et al. ................. 552/521
3,629,298 12/1991 Rheenen ............................. 552/521

Primary Examiner—Howard T. Mars
Assistant Examiner—Kimberly J. Kestler
Attorney, Agent, or Firm—Woodcock Washburn Kurtz Mackiewicz & Norris

[57] ABSTRACT

An aminosterol antibiotic, (3$\beta$(N-[3-aminopropyl]-1,4-butanediamine)-7$\alpha$,24$\zeta$-dihydroxy-5$\alpha$-cholestane 24-sulfate), which can be isolated from the stomach of the common dogfish shark, *Squalus acanthias*, is disclosed.

4 Claims, 5 Drawing Sheets

AMINOSTEROL ANTIBIOTIC

BACKGROUND OF THE INVENTION

This invention relates to a substantially pure aminosterol antibiotic which can be isolated from the tissues of the common dogfish shark, *Squalus acanthias*.

Over the past several years, antibiotic agents have been isolated from a side range of animal species. These agents are believed to play a role in the innate immunity of an animal (Boman, H. G., *Cell* 65, 205–207 (1991)), and comprise a variety of antibiotic substances used in defense against environmental microbes. In certain physiological settings antibiotics are discharged onto epithelial surfaces (Bevins, C. L. et al., *Annu. Rev Biochem.* 59, 395–414 (1990); Samakovlis, C., et al., *EMBO J.* 10, 163–169 (1991); Nicolaides, N., *Science,* 19–26 (1974)), secreted into internal body fluids (Boman, H. G., et al., *Annu. Rev. Microbiol.* 41, 103–126 (1987)), or utilized within the vacuoles of phagocytic defensive cells (Lehrer, R. I., *Cell* 64, 229–230 (1991)). To date, only a limited number of low molecular weight antibiotics have been identified in animals, including peptides (Steiner, H. et al., *Nature* 292, 246–248 (1981); Ganz, T., et al., *J. Clin. Invest.* 76, 1427–1435 (1985); Zasloff, M., *Proc. Natl. Acad. Sci. USA* 84, 5449–5453 (1987)), bacteriostatic alkaloids (Daly, J. W. et al., *Toxicon* 25, 1023–1095 (1987); Preusser, H. J., et al., *Toxicon* 13, 285–289 (1975)), and lipids (Kabara, J. J., *Lipids* 12, 653–659 (1987); Bibel, D. J. et al., *J. Invest. Dermato.* 92, 632–638 (1989); Tiffany, J. M. et al., *Lipid Res.* (eds. Paoletti, R. and Kritchevsky, D.) 22, 1–62 (1987); Brissette, J. L. et al., *J. Biol. Chem.* 261, 6338–6345 (1986).

SUMMARY OF THE INVENTION

It has now been found that the stomach of the dogfish shark, Squalus acanthias, contains abundant amounts of a non-peptidyl broad spectrum antibiotic, active against gram-positive and gram-negative bacteria, fungi, and protozoa. Structural determination of the antibiotic, (3β(N-[3-aminopropyl]-1,4-butanediamine)-7α,24ζ-dihydroxy-5α-cholestane 24-sulfate), reveals it to be an amphipathic cationic steroid, characterized by a condensation of a bile salt intermediate with spermidine, having the structure (in its fully ionized form):

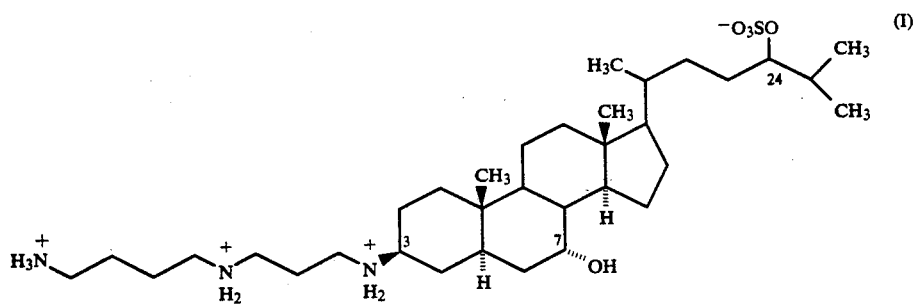

This invention, therefore, relates to substantially homogenous compositions of the compound of formula I, to pharmaceutically acceptable salts of the compound of formula I, to pharmaceutical compositions comprising an effective antibiotic amount of the compound of formula I or a salt thereof, and to methods of treating microbial infections in human or non-human animals comprising administering to said animal an effective antibiotic amount of the compound of formula I or a salt thereof.

DETAILED DESCRIPTION OF THE INVENTION

Antibiotic activity from the stomach of the dogfish was isolated following a modification of a procedure used previously in the isolation of peptide antibiotics from Xenopus stomach. See, Moore, K. S., et al., *J. Biol. Chem.* 266, 19851–19857 (1991). Antimicrobial activity was assayed using E.coli and purified through a series of steps involving organic extraction, size exclusion chromatography, and reversed phase and cation-exchange HPLC. At the final stage of purification (FIG. 1d), only one molecular species could be detected by thin layer chromatography (TLC) using iodine, ninhydrin and charring detection methods. An aqueous solution of squalamine (approximately 0.5 mM) had no absorbance between 220 nm through 700 nm, demonstrating the absence of aromatic moieties, peptide bonds, linear conjugated systems and other chromophores. Retention of the activity on the cation exchange column (FIG. 1c) demonstrated that the molecular species must exhibit a net positive charge at pH 3.

Figure 2A:
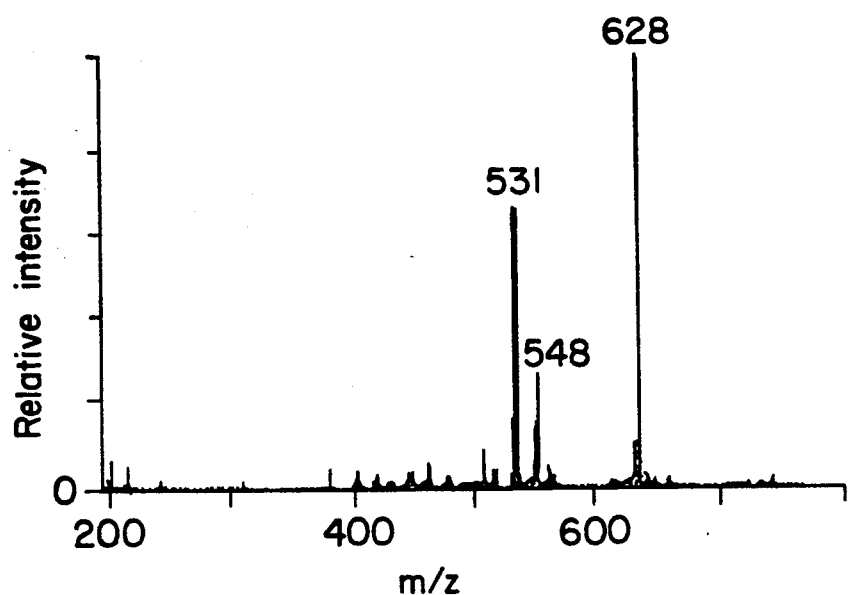
FIGS. 2a and 2b are FAB (fast-atom bombardment) mass spectra and FIGS. 2c and 2d are NMR spectra for squalamine.

The chemical structure of squalamine was determined by FAB mass spectroscopy and nuclear magnetic resonance spectroscopy (NMR). The FAB mass spectrum, in the positive ion mode, yielded a simple fragment pattern, characterized by a molecular ion of 628 atomic mass units (amu) (FIG. 2a). Secondary species were detected at 548 amu and 530 amu, consistent with the loss of a $SO_3$ ion (80 amu) alone, or in addition to water (18 amu), respectively. Measurement of the mass of the molecular ion yielded a value of 628.4739, consistent with an elemental composition of $C_{34}H_{66}O_5N_3S_1$.

Figure 2B:
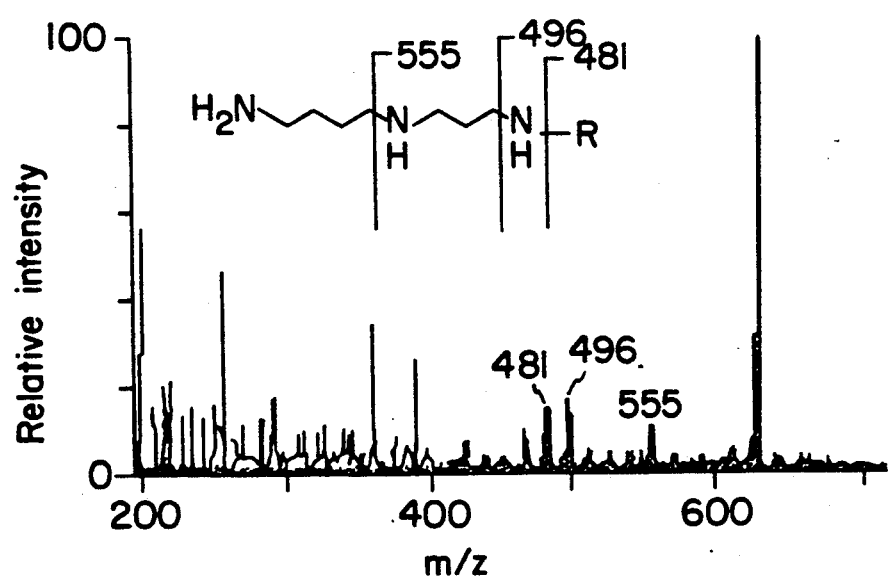

In the negative ion mode, a more complex mass spectrum was obtained, characterized by a strong molecular ion at 626 amu (FIG. 2b).

Figure 2C:
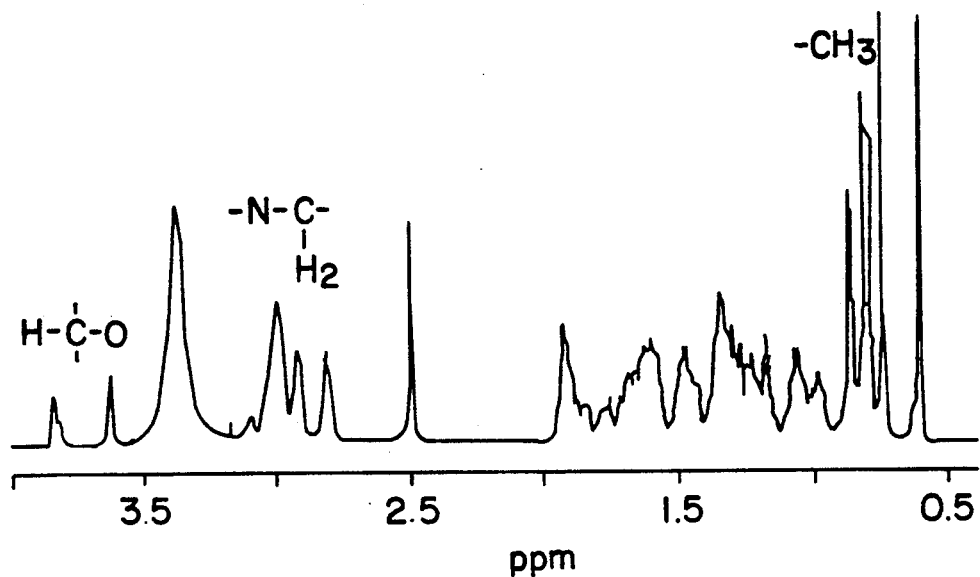

The chemical structure of squalamine was studied by proton and $^{13}C$ NMR, using one and two dimensional techniques (FIG. 2c,d). In dimethylsulfoxide, squalamine exhibited a proton spectrum characteristic of a steroid (0.5–2.5 ppm), and a molecule of spermidine (3.05–3.3 ppm). Two dimensional correlation spectroscopy permitted assignment of all chemical shifts and established that the steroid contained an α-AB ring junction. Positions of the free OH on the C-7, the sulfate on the C-24, and the spermidine on C-3 were established unambiguously by the complete analysis of the TOCSY, COSY and NOESY 2D spectra. The specific amino group of the spermidine involved in coupling to the steroid nucleus was deduced by NMR analysis (FIG. 2c,d) and confirmed by the mass spectrum obtained in the negative ion mode (FIG. 2b), which revealed ions of mass 481, 496 and 555, consistent with fragments generated by the loss of all or portions of the spermidine moiety (FIG. 2b).

The deduced structure of the antibiotic isolated from shark stomach is as shown above (in fully ionized form) in FIG. 1. The molecule has a steroid ring structure like cholestanol. Spermidine is coupled to the C-3 position, replacing the usual steroid hydroxyl or ketone group. In addition, hydroxylation is seen at positions C-7 and C-24, and the C-24 hydroxyl is sulfated. The stereochemistry of the junction between rings A and B in squalamine (5-α) is seen commonly in bile alcohols of many species of fish. (Haslewood, G. A. D., *J. Lipid Res.* 8, 535–550 (1967); Tammer, A. R. in *Chemical Zoology* (eds. Florkin, M. and Scheer, B. T.) Vol. 8, 595–612 (1974)) Consistent with the deduced structure of squalamine, antibiotic activity was demonstrated to be resistant to boiling and protease treatment.

A substantially homogeneous composition of squalamine, the compound of Formula I, may be prepared via the purification and isolation methods described above and described in more detail in Example 1. By "substantially homogeneous", as used herein, is meant a composition that is greater than about 95% pure, as shown by thin layer chromatography and NMR.

Pharmaceutically acceptable salts of squalamine may be prepared by methods well known in the art. Such salts include, but are not limited to, sodium, potassium, ammonium and chloride salts.

The squalamine described herein appears to be without precedent in the animal kingdom. Although bile alcohol sulfates are present in fish, no molecule such as squalamine has been reported in fish or other marine animals. A review of the chemical structures of naturally occurring aminosterols revealed the similarity of squalamine to several cationic steroids isolated from medicinal plants used in the treatment of intestinal parasitic infections. See Rahman, A. -U., *Handbook of Natural Products Data* (Elsevier Science Publishers B. V., Amsterdam, 1990). For example, squalamine resembles the antiparasitic aminosterol chonemorphine, from the Indian plant, Chonemorpha fragrans. (Shah, V. G., et al., *Steroids* 53, 559–565 (1989)). This molecule has the identical steroid ring system as squalamine, with a primary amino group at C-3; however, it differs due to the presence of a second amino group on a shortened cholesterol side chain, and by the absence of a hydroxyl moiety or an anionic substituent.

The test results presented below suggest that squalamine has a broad range of potent antibiotic activity against a plurality of microorganisms including gram-positive and gram-negative bacteria, fungi, protozoa and the like. Hence, squalamine provides a method of treating or controlling microbial infection caused by those organisms which are sensitive to squalamine. Such treatment comprises administering to a host or tissue susceptible or afflicted with microbial infection an antimicrobial amount of squalamine. Due to its antibiotic properties, squalamine may also be used as a preservative or sterilant of materials susceptible to microbial contamination.

Pharmaceutical compositions comprising squalamine as an active ingredient in an amount sufficient to produce antibiotic effect in susceptible host or tissue and a pharmaceutically acceptable, non-toxic sterile carrier can be prepared. An effective antibiotic dose of squalamine would vary from patient to patient, and infection to infection, but it is expected that such a dose would be in the range of about 10 to about 100 mg/kg. Suitable pharmaceutical carriers, which include fillers, non-toxic buffers, physiological saline solution and the like, are well known in the art and described, for example, in Remington's Pharmaceutical Sciences, E. W. Martin, a standard reference text in this field. The composition may be used topically or systemically and may be in any suitable form such as liquid, solid, semi-solid, which include injectable solutions, tablets, ointments, lotions, pastes, capsules and the like. The squalamine may also be administered in combination with other adjuvants, protease inhibitors, or compatible drugs where such combination is seen desirable or advantageous in controlling the infection caused by harmful microorganisms, including protozoa, viruses and the like.

Although not intending to be bound by any theory, squalamine is assumed to exert its antibiotic activity by perturbing membrane permeability. From the chemical structure of squalamine, it is envisaged as a "nascent" detergent. In water, the sulfate bearing side chain and the spermidine moiety are free and unconstrained. As such, the molecule should not exhibit a fixed dipole moment or a fixed spatial segregation of polar and apolar domains characteristic of membrane-disruptive detergents. In a medium of low dielectric constant, however, it is imagined that electrostatic interactions between the terminal amino group of the spermidine and the sulfate on C24 would bring the side chains together to form a "handle" over the flat steroid ring structure, resulting in a basket-like secondary structure: A hydrophilic handle situated over a hydrophobic basket. The molecule would now exhibit a definite polarization of hydrophilic and hydrophobic residues. A similar transformation characterizes magainin peptides, which exhibit little secondary structure in water but organize into an amphipathic α-helix upon binding to a membrane. The spermidine moiety would appear to permit squalamine to bind to membranes composed of negatively charged phospholipids, characteristic of bacterial lipids, providing the same basis of selectivity as explained for other cationic antibiotic membrane-perturbing agents, such as magainin.

The following examples are provided to illustrate the isolation, activity and biodistribution of squalamine.

EXAMPLE 1

Isolation of Squalamine

Figure 1A:
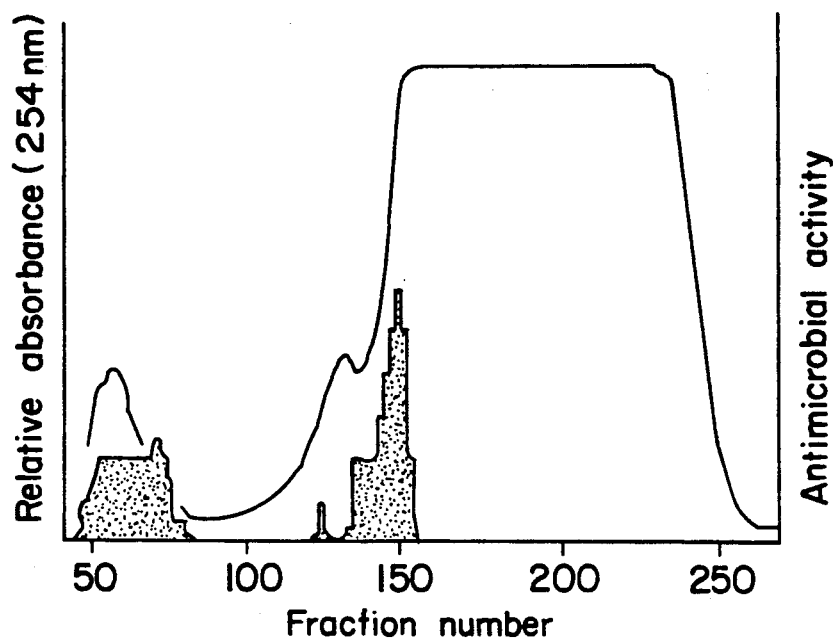
FIG. 1 is a series of spectra illustrating steps in the isolation of squalamine from dogfish stomach.

Squalus acanthias sharks were captured off of the New England coast. The shark stomach tissue (400 g) was frozen immediately following dissection, pulverized in liquid nitrogen and extracted with five volumes of 60% acetonitrile, 1% trifluoroacetic acid (TFA) for several days. After centrifugation at 8,000 rpm in a Sorvall GS3 centrifuge (DuPont, Wilmington, Del.) for 30 minutes, the supernatant was lyophilized, and resuspended in 250 ml of 0.1% TFA. Next, the sample was extracted by a modification of the Folch (Folch, J., et al., *J. Biol. Chem.* 226, 497–509 (1957); Roos, D. S. et al., *J. Cell. Biol.* 101, 1578–1590 (1985)) method: 15 vol of chloroform-methanol (2:1) was added and the resulting precipitate removed; to the organic phase 0.2 vol of 0.1M KCl in $H_2O$ was added, and the two phases allowed to separate after vigorous mixing. The aqueous phase was recovered and lyophilized, resuspended in 30 ml of $H_2O$, then loaded onto a 45×5 cm Bio-Gel P-30 (Bio-Rad, Richmond, Calif.) gel filtration column in 0.1% TFA, 20% acetonitrile. The fractions were dried under vacuum, resuspended in water and assayed as described previously. (Moore, K. S., et al., *J. Biol. Chem.* 266, 19851–19857 (1991)) FIG. 1a shows the absorbance at 254 nm for fractions from the P-30 gel filtration column, and the histogram indicates the relative antimicrobial activity against *E. coli* $D_{31}$.

Figure 1B:
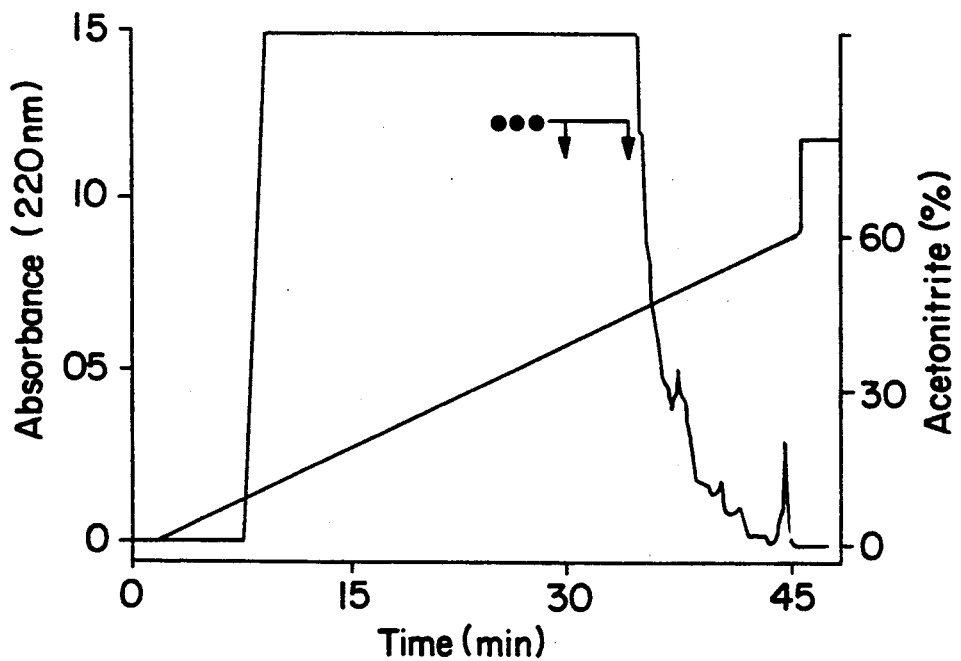

Active fractions containing low molecular weight molecules (500–1,000 daltons) were pooled and run on a $C_{18}$ reversed-phase HPLC column (4.6×220 mm, Aquapore OD-300, Applied Biosystems, San Jose, Calif.). After flushing the column extensively and allowing the absorbance to return to baseline, the column was eluted with a linear gradient of 0–60% in 45 minutes at a flow rate of 1 ml/min with buffer A (0.1% TFA in $H_2O$) and buffer B (0.08% TFA in acetonitrile). The results are shown in FIG. 1b in which (as in FIGS. 1c and 1d) the light line shows absorbance at 220 nm, the heavy line shows the buffer gradient, and the dots indicate minor antimicrobial activity against *E. coli* $D_{31}$. The bracket with the arrows indicates the major antimicrobial peak which was pooled for the next step of purification.

Figure 1C:
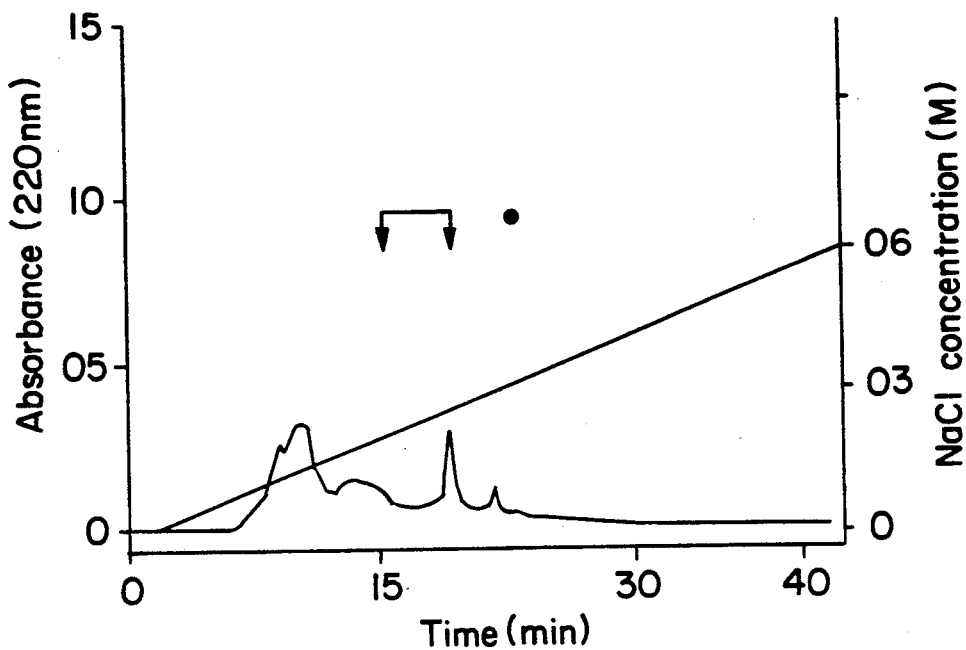
Figure 1D:
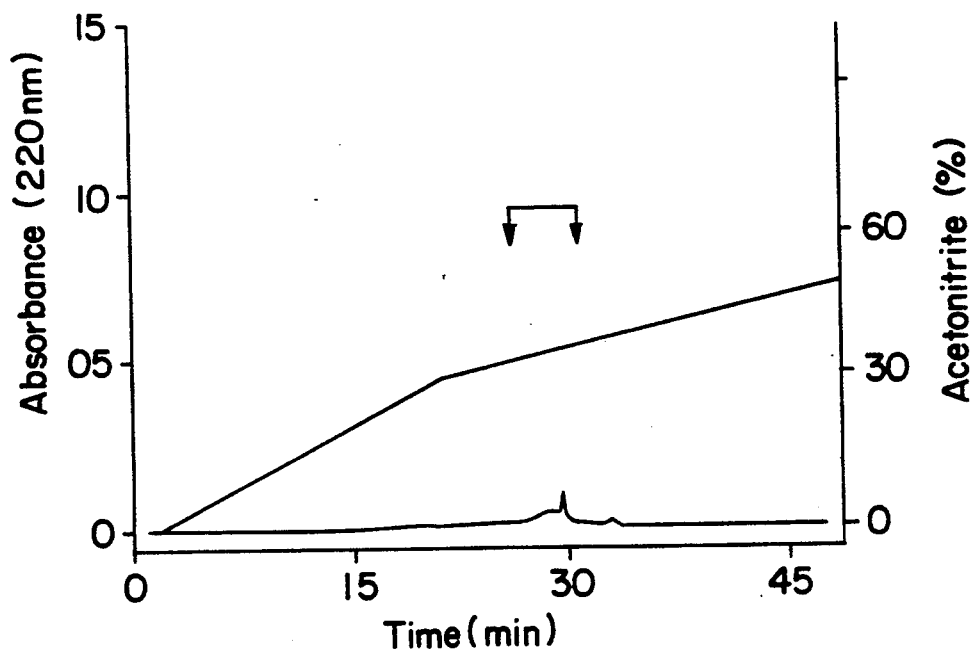

Fractions containing the main peak of activity were then run on a strong cation-exchange HPLC column (4.5×200 mm, 5 μm, 300 A, polysulfoethyl aspartamide, Poly LC, Columbia, Md.), after first flushing the column extensively, as above, and allowing the absorbance to return to baseline. Results are shown in FIG. 1c. The gradient was 0–60% in 45 minutes at 1 ml/min with buffer A (5 mM $KH_2PO_4$, pH 3, 25% acetonitrile) and buffer B (5 mM $KH_2PO_4$, pH 3, 25% acetonitrile, and 1M NaCl).

The fractions containing the main peak of activity were then run on a $C_4$ reversed phase HPLC column (4.6×25 mm, 5 mm, Vydac, The Separations Group, Hesperia, Calif.) with the same buffers as used for the $C_{18}$ column. The gradient was 0–30% in 20 minutes followed by 30–50% in 30 minutes. See FIG. 1d.

The purified squalamine sample was alkalinized with sodium hydroxide, then applied to a silica gel 60 thin layer chromatography plate (Merck, Darmstadt, Germany), and developed with a solvent of isopropanol-acetonitrile-$H_2O$-acetic acid (68:10:68:4). Only one band, ($R_f$=0.12) was detected by iodine, ninhydrin and charring detection methods.

FIG. 2a is the FAB mass spectra of squalamine, positive-ion mode, and FIG. 2b is the FAB mass spectra of squalamine, negative-ion mode. The insert in FIG. 2b shows the spermidine substituent with lines indicating fragments of the molecule which are consistent with the observed ions. R is 7α, 24 ζ -dihydroxy-5α-cholestane 24-sulfate. The FAB analysis was carried out on a VG Analytical ZAB 2-SE high field mass spectrometer operating at an acceleration voltage of 8 kV. A cesium ion gun was used to generate ions for the acquired mass spectra which were recorded using a PDFF 11-250J data system. Mass calibration was performed using cesium iodine. Sample analysis was performed using a matrix of glycerol:thioglycerol 1:1 (v/v).

FIG. 2c is a proton NMR spectrum of squalamine. Squalamine solution (2 mM) in DMSO (310° K) was examined at 600 MHz on a Bruker AM 600 spectrometer (Bruker, Karlsrhue, Germany). Signals between 0.5 and 2.0 ppm included steroid protons. Signals between 2.8 and 3.1 ppm correspond to the—$NCH_2$ protons of spermidine. The conditions utilized were: 16 scans, SW−2,500 hZ, SI 4K, 2 sec. repetition, 90° pulse flip angle.

Figure 2D:
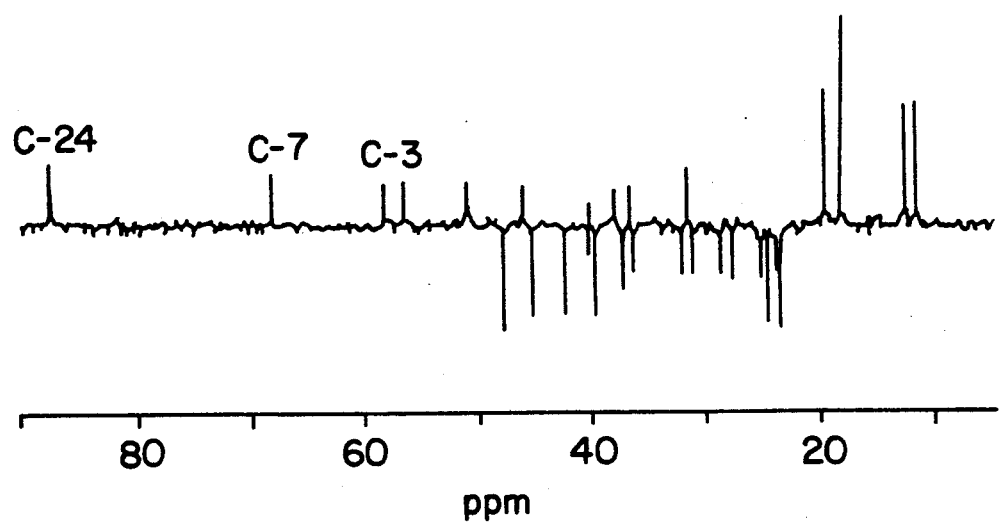

FIG. 2d is a $^{13}$DEPT NMR spectrum of squalamine. Squalamine solution (6 mM) in $D_2O$, pH 2.3 (310° K) was examined at 100.62 MHz on a Bruker AM 400 spectrometer (Bruker, Karlsrhue, Germany). The conditions utilized were: 32K data points, SW=25 KHz, 43,000 scans. Peaks have been phased such that CH, $CH_3$ are positive, and the $CH_2$ resonances are negative. (Doddrell, D. M. et al., *J. Mag. Res.* 48, 323 (1982); Doddrell, D. M. et al., *J. Chem. Phys.* 77, 2745 (1982)). Two additional resonances, corresponding to the two quaternary carbons (at 36.15 and 43.18 ppm), visible on the 1D$^{13}$C CpD spectrum, have been suppressed by the pulse sequence. The position of the spermidine on C-3, the $OSO_3$ pm C-24, and the OH on C-7 were deducted from analysis of 2D TOCSY, COSY and NOESY experiments. The complete assignments were obtained from the studies above as well as HMQC 1J and 3J experiments. The α-AB ring junction was deduced from the $^{13}$C chemical shifts of the two quaternary carbons, and the two methyl groups (C-18 and C-19) by comparison with the published spectra of α and β cholestane. (Reich, H. J. et al., *J. Amer. Chem. Soc.* 91, 7445 (1969); Balogh, B., et al., *Nature* 233, 261 (1971)).

EXAMPLE 2

Antimicrobial Activity of Squalamine

Squalamine was assayed in vitro against several microbial organisms to evaluate its spectrum of activity.

Minimal inhibitory concentrations for the bacteria and yeast were determined by incubating 0.9–11×$10^5$ colony-forming units/ml of log-phase organisms in ½×tryptica soy broth (TSB) with increasing concentrations of sample in static 96-2311 microtiter plates (Corning, Inc., Corning, N.Y.) at 37° C. for 18 to 24 hours. The minimal inhibitory concentration is the concentration of sample at which no growth was observed. Control incubation in the absence of bacteria served to set a baseline value.

Initial sample concentrations were 2 mg/ml in 250 mM sodium acetate pH 6.6, 11.2 mM HCl, except taurolithocholic acid 3-sulfate which was 2 mg/ml in 50 mM sodium acetate, and squalamine to which HCl was not added because it was acidic following the last step of purification. Spermidine HCl, taurolithocholic acid 3-sulfate, melittin, holothurin and ampicillin were purchased from Sigma (St. Louis, Miss.). CHAPS (3-[(3-cholamidopropyl)dimethylammonio]-1-propane sulfonate dihydrate) was purchased from Aldrich (Milwaukee, Wis.). Conessine was purchased from Aldrich Rare Chemicals Division (Milwaukee, Wis.). Magainin-II amide and CPF-amide were made by Magainin Pharmaceuticals, Inc. (Plymouth Meeting, Penn.). The CPF peptide used in the assay has the sequence GFGSFLGKALKAALKIGANALGGSPQQ-$NH_2$. (Richter, K., et al., *J. Biol. Chem.* 261, 3676–3680 (1986).

Minimal disruptive concentration (the concentration at which physical disruption of the protozoa occurred) was determined for the protozoa by adding 15 ml of sample (in sodium acetate as above) to 100 ml of 1% trypticase soy broth containing *P. caudatum* (Nasco, Fort Atkinson, Wiss,). Organisms were observed by light microscopy for ten minutes.

The activity of squalamine is shown in comparison with several other related molecules in Table I.

TABLE I

| (Minimal Inhibitory Concentration, µg/ml) | | | | |
|---|---|---|---|---|
| ATCC# | E. coli (25922) | Staph. aureus (29213) | Pseudomonas aeruginosa (27853) | Strep. faecalis (29212) |
| Shark | 1-2 | 1-2 | 4-8 | 1-2 |
| CHAPS | >500 | >500 | >500 | 250-500 |
| Taurolithocholic Acid 3-sulfate | >500 | >500 | >500 | >500 |
| Spermidine | >500 | >500 | >500 | 250-500 |
| Melittin | 8-16 | 8-16 | 16-31 | 4-16 |
| Magainin II | 31-62 | >250 | 31-62 | >250 |
| Ampicillin | 2-4 | 1 | 62-125 | <0.25 |
| Conessine | >500 | >500 | >500 | >500 |
| CPF | 8-16 | 8-16 | 8-31 | 31-62 |
| Holothorin | >500 | >500 | >500 | >250 |
| ATCC # | Candida albicans (14053) | Proteus vulgaris (13315) | Serratia marcescens (8100) | Paramecium caudatum |
| Shark | 4-8 | 4-8 | >125 | 4-8 |
| CHAPS | >500 | >500 | >500 | >260 |
| Taurolithocholic Acid 3-sulfate | >500 | >500 | >500 | >260 |
| Spermidine | >500 | >500 | >500 | >260 |
| Melittin | 16-31 | 16-31 | >250 | 2-4 |
| Magainin II | 125-250 | 125-250 | >250 | 33-65 |
| Ampicillin | >125 | 8-16 | 4-62 | >65 |
| Conessine | 31-62 | >500 | >500 | 16-33 |
| CPF | 62-125 | 62-125 | >125 | 4-8 |
| Holothorin | >500 | >500 | >500 | 130-260 |

As seen in Table I, squalamine compares in antibacterial potency to ampicillin and is somewhat more potent than the Xenopus antimicrobial peptides against magainin II-amide and CPF (caerulein precursor fragment). Conessine, an alkaloid of plant origin, used therapeutically as an antiparasitic agent, exhibits antifungal (Candida) and antiprotozoan (*Paramecium caudatum*) activity, but lacks antibacterial activity, demonstrating that potent antibiotic activity is not a trivial property of all cationic steroids. Holothurin, a steroid glycoside from the sea cucumber (Burnell, D. J. et al., *Marine Natural Products: Chemical and Biological Perspectives* (ed Scheuer, P.J.) Vol. 5, 287-379 (1983)), exhibits modest anti-protozoan activity, but is without antibacterial or antifungal activity, demonstrating that surface-active steroids of the saponin family are not comparable to squalamine in biological activity. Spermidine itself is inactive as an antibiotic in the concentration range studied, as is the anionic bile salt taurolithocholic acid 3-sulfate, and the synthetic zwitterionic steroidal detergent CHAPS. These data suggest that the biological activity of squalamine results from the synergistic combination of an anionic bile salt with spermidine, each of which independently exhibits considerably less antibiotic activity than squalamine.

The importance of the amine substitution on the steroid ring of squalamine for its antibiotic activity is supported by recent studies. The synthesis of a common bile acid (e.g., deoxycholic acid) containing a basic group has been shown to impart the steroid with unexpected antibiotic activity. (Bellini, A. M. et al., *Eur. J. Med. Chem.—Chin. Ther.* 18, 185-190 (1983); Bellini, A. M. et al *Eur. J. Med. Chem.—Chin. Ther.* 18, 190-195 (1983); Bellini, A. M. et al., *Arch. Pharm (Weinheim)* 323, 201-205 (1990)) The potency and antibiotic spectrum of these synthetic amino-bile acids appear to be dependent on both the structure of the ring system as well as the position and nature of the amine substituents. In particular, addition of an amine substituent onto the C-3 position of the deoxycholate ring system appears to markedly enhance antibiotic activity, although these derivatives exhibit a spectrum primarily against gram positive bacteria. Amine substitutions also dramatically reduce both hepatic clearance of these modified bile acids from the bloodstream and their secretion into bile (Anwer, M. S. et al., *Am. J. Physiol.* 249, G479-G488 (1985)), and might be expected to alter their systemic biodistribution compared to bile salts.

EXAMPLE 3

Hemolysis

Because of its structural resemblance to steroidal detergents, squalamine was assayed for its hemolytic activity against human erythrocytes.

Each sample was diluted in $H_2O$ and was added to a 10% (vol/vol) suspension of human erythrocytes in phosphate buffered saline (PBS). Erythrocytes were collected with heparin and washed once in 1×PBS before the assay. Samples were incubated at 37° C. for ten minutes, centrifuged at 12,000× g for one minute, and the $OD_{350}$ of the supernatant was measured. Addition of Triton X-100 (final concentration 0.1%) defined 100% hemolysis. Data are presented in FIG. 3.

Although squalamine exhibits some hemolytic activity, it occurs at higher concentrations than observed for a non-selective membrane disruptive amphipathic peptide, such as mellitin. Furthermore, squalamine exerts antibiotic activity at concentrations below which erythrocyte disruption is observed. In contrast, the hemolytic and antibiotic activity of mellitin fall within a similar concentration range. Thus, squalamine exhibits a relative selectivity for microbial cells when compared to mellitin, which acts as through a non-selective membrane-disruptive mechanism.

Figure 3:
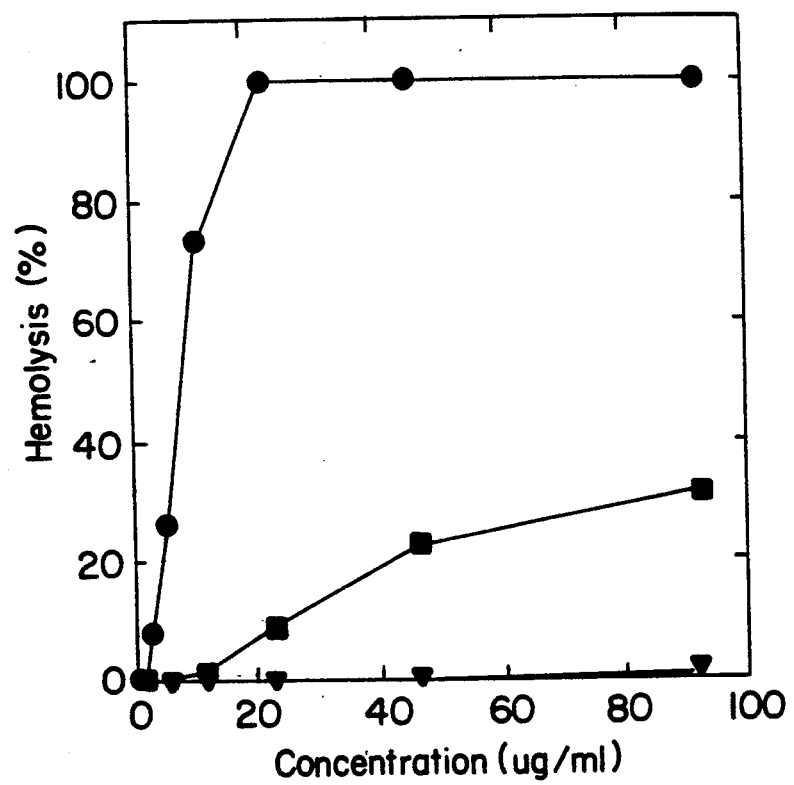
FIG. 3 is a graph showing the results of hemolytic assays of squalamine (squares), mellitin (circles) and magainin-II amide (triangles).

The assayed results of compounds not included in the graph of FIG. 3 are as follows: at 92 µg/ml, CPF showed 3% and holothurin caused 14% hemolysis, while CHAPS and taurolithocholic-acid 3-sulfate, ampicillin, spermidine and conessine all caused <0.5% hemolysis.

EXAMPLE 4

Tissue Distribution

The tissue distribution of squalamine was determined by extraction of freshly obtained tissues of Squalus using the same procedure as described in Example 1 for the stomach extraction. Other *Squalus acanthias* tissues (about 50 g of liver, gallbladder, spleen, testes, gill and intestine) were extracted as above, and purified through the $C_{18}$ HPLC stage. Antimicrobial activity was detected in each tissue, and one reversed-phase fraction from each tissue was analyzed by FAB mass spectroscopy. The yield from the stomach was determined by spotting several dilutions onto a TLC plate and comparing the ninhydrin staining to a spermidine standard curve. The result agreed with the estimate obtained by NMR spectroscopy when the squalamine signal intensity was compared to that of a standard. An estimate of the yield of squalamine from other tissues was made by comparing the antimicrobial activity of reversed-phase fractions to the activity from the stomach.

Squalamine could be detected in many tissues of the shark. The liver and gall bladder, the organs in which bile salts are synthesized and stored for secretion into the GI tract, are the richest sources identified (about 4–7 μg/gm). However, both the spleen and the testes of this animal are also relatively rich sources of squalamine (about 2 μg/gm each). The stomach (1 μg/gm), the gills (0.5 μg/gm), and the intestine (0.02 μg/gm) yielded lesser amounts.

EXAMPLE 5

Heat and Protease Resistance

Squalamine at 0.2 μg/ml in 1×phosphate buffered saline was boiled for fifteen minutes. A 2 μl aliquot of the sample before and after boiling was applied to a lawn of *E. coli* $D_{31}$. Squalamine retained its antimicrobial activity after boiling.

Proteinase K (final concentration 2 mg/ml) was added to 0.2 μg/μl squalamine or 0.8 μg/μl magainin II amide in 1×phosphate-buffered saline. After a one hour incubation at 37° C., 2 μl of each sample was applied to the lawn of *E. coli* $D_{31}$. Magainin-II amide lost all activity on proteinase K digestion, but squalamine retained its activity,

What is claimed is:

1. A substantially homogeneous composition of the compound 3β(N-[3-aminopropyl]-1,4-butanediamine)-7α,24ζ-dihydroxy-5α-cholestane 24-sulfate.

2. A pharmaceutically acceptable salt of the compound 3β(N-[3-aminopropyl]-1,4-butanediamine)-7α,24ζ-dihydroxy-5α-cholestane 24-sulfate.

3. A pharmaceutical composition comprising the compound 3β(N-[3-aminopropyl]-1,4-butanediamine)-7α,24ζ-dihydroxy-5α-cholestane 24-sulfate or a pharmaceutically acceptable salt thereof, and one or more pharmaceutically acceptable carriers or diluents.

4. A method of treating microbial infections in human or non-human animals comprising administering to said animal an effective antibiotic amount of the compound 3β(N-[3-aminopropyl]-1,4-butanediamine)-7α,24ζ-dihydroxy-5α-cholestane 24-sulfate or a pharmaceutically acceptable salt thereof.

* * * * *